(12) United States Patent
Ono et al.

(10) Patent No.: US 6,629,964 B1
(45) Date of Patent: Oct. 7, 2003

(54) STEAM-GENERATING PAD

(75) Inventors: Shigeyuki Ono, Tokyo (JP); Tomoshige Umeda, Tokyo (JP); Kazuya Otsuji, Tokyo (JP); Wataru Okawa, Tokyo (JP); Toru Yoshihara, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/623,521

(22) PCT Filed: Apr. 2, 1999

(86) PCT No.: PCT/JP99/01749
§ 371 (c)(1),
(2), (4) Date: Oct. 3, 2000

(87) PCT Pub. No.: WO99/51174
PCT Pub. Date: Oct. 14, 1999

(30) Foreign Application Priority Data

Apr. 3, 1998 (JP) .............................................. 10-91790
Mar. 3, 1999 (JP) .............................................. 11-56275

(51) Int. Cl.$^7$ ............................... A61F 13/00; A61F 7/00
(52) U.S. Cl. ........................... 604/304; 602/48; 607/96; 607/108
(58) Field of Search .................................. 602/41–59, 2; 607/108–112; 604/304–308

(56) References Cited

FOREIGN PATENT DOCUMENTS

| EP | 0376490 A1 | * | 4/1990 | |
| EP | 0345350 B1 | * | 9/1994 | |
| JP | 63-22915 | | 2/1988 | |
| JP | 64-20818 | | 2/1989 | |
| JP | 7-9318 | | 2/1995 | |
| JP | 11-137591 | | 5/1999 | |
| WO | WO 95/20415 | * | 8/1995 | .................. 602/41 |

* cited by examiner

Primary Examiner—Kim M. Lewis
(74) Attorney, Agent, or Firm—Oblon, Spivak, McClelland, Maier & Neustadt, P.C.

(57) ABSTRACT

A steam-generating unit that is applied to the skin or the mucous membranes has a steam-generating part that employs chemical energy, and the surface applied to the skin or mucous membranes is made from a moisture-permeable sheet. The temperature of the steam generated by the steam-generating part and released from the surface of the steam-generating unit is kept to 50° C. or lower. Steam that is as safe as that from a steam towel can be easily and continuously supplied to the skin and mucous membranes by this steam-generating unit.

7 Claims, 4 Drawing Sheets

10A (x − x CROSS SECTION)

10A (x – x CROSS SECTION)

10B (x – x CROSS SECTION)

10C (x-x CROSS SECTION)

10D (x-x CROSS SECTION)

10E (x - x CROSS SECTION)

10F (x - x CROSS SECTION)

10G

STEAM-GENERATING PAD

TECHNICAL FIELD

The present invention pertains to a steam-generating unit that provides steam to the skin of body parts, including the scalp, shoulders, neck, face, hips, buttocks, feet, hands, arms, etc., and mucous membranes, such as the eyes, nose, throat, etc., and thereby moistens these body parts and mucous membranes. In particular, the present invention pertains to a steam-generating unit with which it is possible to efficiently percutaneously absorb drug and cosmetic components through steam and heat when it is used patched to the skin.

BACKGROUND ART

Facial saunas, steam towels, etc., are being used to provide steam that has been optimally heated to the skin and thereby promote skin circulation and keep the skin in the desired moisturized state, or improve the moisturized state of the skin.

Nevertheless, facial saunas and steam towels cannot always be used at any time and at any place. Moreover, it is difficult to use facial saunas for any part of the body other than the face. Furthermore, steam towels also pose a problem in that the time for which they can provide sufficient steam is short.

The method whereby steam is generated using an electric heater or ultrasonic waves is also a method of providing steam. However, this method cannot always be used everywhere. Moreover, there are also methods that employ chemical energy, such as the heat of neutralization of acids and alkalis, the heat of hydration of inorganic salts, the heat of oxidation of metal powders, such as iron powder, etc., but since temperature of the steam that is generated is not controlled, even if these methods are simply used, there is a problem in terms of safety when they are directly used on the body.

The purpose of the present invention is to make it possible to easily and continuously provide steam that is just as safe as that from a steam towel to the skin and mucous membranes in response to these types of problems with background art.

DISCLOSURE OF THE INVENTION

In order to accomplish the above-mentioned purpose, the present invention presents a steam-generating unit, characterized in that it is a steam-generating unit that has a steam-generating part that uses chemical energy and that is suitable for application to the skin and mucous membranes, and in that the temperature of steam that is released from the surface of said steam-generating unit is kept to 50° C. or Lower.

As a preferred mode of the above-mentioned type of steam-generating unit, a steam-generating unit where the amount of steam released from the surface of the steam-generating unit applied to the skin or mucous membranes is 0.01 mg/cm$^2$·min or more, particularly 0.5 mg/cm$^2$·min or more is presented.

Moreover, a mode of the above-mentioned type of steam-generating unit where cosmetic component or drug is placed on its surface or on the inside, and a mode where an adhesive layer is formed on the surface of the steam-generating unit that will be patched to the skin is presented.

The steam-generating unit of the present invention uses chemical energy in its steam-generating part and therefore, when compared to the case where steam is generated with a facial sauna, an electric heater or ultrasonic waves, moisture and heat can be provided to the skin and mucous membranes of any part of the body, easily and at any time. Furthermore, since the temperature of the steam that is released from the surface of the steam-generating unit is kept at 50° C. or lower, it can be used comfortably and safely.

Moreover, a sufficient amount of steam can be provided to the skin and the mucous membranes by the mode where the amount of steam that is released from the surface of the steam-generating unit applied to the skin or mucous membranes is kept at 0.01 mg/cm$^2$·min or more, preferably 0.5 mg/cm$^2$·min or more.

Furthermore, by means of the mode whereby there is a cosmetic component or drug at the surface or inside the steam-generating unit and this cosmetic component or drug is released with the steam, the skin can be more quickly moisturized by the steam that is provided from the steam-generating unit than the moisture that is provided by simple perspiration, and penetration of the cosmetic component or drug to the skin is promoted, and the moisturized state is retained for a long period of time, enhancing the effects of these cosmetic components and drugs.

In addition, by means of the mode where an adhesive layer that makes it possible to patch the steam-generating unit to the skin is formed, a separate holder, etc., is not necessary when the steam-generating unit is used on the skin and therefore, the steam-generating unit can be very easily used.

BEST MODE FOR CARRYING OUT THE INVENTION

Figure 1A:
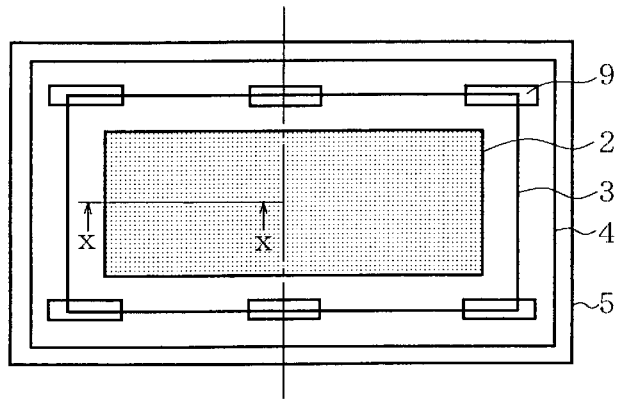
FIG. 1A is a top view of the steam-generating unit and FIG. 1B is a cross section of it.

The present invention will now be explained in detail.

The steam-generating unit of the present invention is used on the skin of the parts of the body, such as the scalp, shoulders, neck, face, hips, buttocks, feet, hands, arms, etc. and mucous membranes, such as the eyes, nose, throat, etc.

Here, applying the steam-generating unit to the skin or mucous membranes can mean both bringing the steam-generating unit into contact with the skin or mucous membranes by patching the steam-generating unit to the skin or mucous membranes, and placing the steam-generating unit close to the skin or mucous membranes without making contact.

Moreover, the steam that is released from the steam-generating unit of the present invention can be both gasified water and fine water droplets.

One characteristic of the steam-generating unit of the present invention is that chemical energy is used in the steam generating part.

Heat of neutralization of acids and alkalis, heat of hydration of inorganic salts (calcium chloride, magnesium chloride, calcium oxide, magnesium oxide, zeolite, etc.), heat of oxidation of metal powder, etc., can be mentioned as the chemical energy here.

The actual mode of use of said chemical energy in the steam-generating part is determined as needed in accordance with the type of reaction of the chemical energy that will be used. For instance, when the heat of neutralization of an acid and an,alkali or the heat of hydration of an inorganic salt, etc., is used, the steam generating part can be constructed from a heating part that generates the heat of neutralization or heat of hydration and a vaporizing part where steam is released by the heat generated from the heating part. In this case, the heating part can be made so that the reactants themselves that are to react are separated by a partition and whenever steam is generated, this partition is broken down so that the reaction will proceed. Moreover, the vaporizing part is, for instance, made from a fiber aggregate of paper, fabric, nonwoven fabric, etc., or a porous material impregnated with water so that steam is released when heat is generated by the heating part.

Of the modes of using chemical energy, the mode where the exothermic body itself releases steam is preferred because a vaporizing part that is separate from the heating part is not needed. An example of this is a steam-generating composition that comprises metal powder, salt, and water and releases steam with oxidation of the metal powder. In more concrete terms, for instance, iron powder goes through an exothermic reaction as shown by the following formula

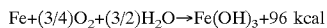

$$Fe+(3/4)O_2+(3/2)H_2O \rightarrow Fe(OH)_3 + 96 \text{ kcal}$$

to release the water within the system as steam.

This type of exothermic reaction by metal powder is used in what is called a chemical pocket heater. General chemical pocket heaters are constructed basically as heat tools and therefore, there are concerns about whether they will have optimal gas permeability and whether the water needed for the reaction will not escape from them. Therefore, bags holding exothermic composition of chemical pocket heaters have gas permeability, but in the end, they are not made from a sheet that is moisture permeable. For instance, a sheet with a moisture permeability of 100~400 $g/m^2 \cdot 24$ h by ASTM methods (Method E-96-80D) is used in Japanese Patent Laid-Open No. 1-250252. In contrast to that, since the steam-generating composition of the present invention is ultimately used as steam generation source, the surface that is applied to the skin or mucous membranes is made from sheet with a moisture permeability of preferably 4,000 $g/m^2 \cdot 24$ h or more, more preferably 8,000 $g/m^2 \cdot 24$ h or more, and therefore, the method of using the steam-generating composition of the present invention is very different from the method whereby the same composition in the conventional chemical pocket heaters is used.

Furthermore, it is a known fact that steam is released to outside the system with the exothermic reaction of the above-mentioned composition, and exothermic units for curling hair that use these steam-generating effects and heating effects (Japanese Patent Laid-Open No. 62-172907) are common. Nevertheless, the temperature of the steam that is to be released during the exothermic reaction by the above-mentioned composition becomes 60° C. or higher when it is exposed to the atmosphere, or almost exposed to the atmosphere, because the amount of air that passes to the composition cannot be controlled. If the subject of application is hair, there is no problem with steam that is 60° C. or higher, but the skin and mucous membranes may be damaged by steam at 60° C. or higher provided continuously. Therefore, by means of the present invention, steam that is kept at 50° C. or lower is provided to the skin and mucous membranes.

By means of the present invention, this type of temperature control is also performed when chemical energy in the form of the above-mentioned heat of neutralization of acids and alkalis, heat of hydration of inorganic salts, etc., is employed.

Furthermore, in order to keep the temperature of the steam that is released from the steam-generating unit at 50° C. or lower, the temperature of this steam is determined under atmosphere at room temperature (25° C., 65% RH), by placing the steam-generating unit with its steam-generating surface facing up on a pedestal of expanded polystyrene, setting the detector of a temperature gauge (Thermorecorder RT-10 made by Tabaiesupekku Co., Ltd.) on this surface so that weight is-not applied to the steam-generating unit, and determining the temperature at the surface of the steam-generating unit for 15 minutes.

Moreover, by means of a different method, temperature is determined in accordance with the method of determining the temperature of disposable pocket heaters of JIS S4100, which is more resemble to an actual system. This temperature determination method shows a temperature that is higher than the temperature obtained by the above-mentioned determination method, as will be shown in the following examples, and therefore, the temperature of the steam that is released from the surface of the steam-generating unit is kept at 50° C. or lower in this case as well.

One mode of temperature control is a temperature-regulating material placed between the steam-generating part and the surface of the steam-generating unit so that the steam released from the steam-generating part passes through the temperature-regulating material and the steam temperature is reduced. Controlling temperature with a temperature-regulating material is preferred because temperature of the steam that is released from the surface of the steam-generating unit can be reliably and simply controlled to 50° C. or lower, regardless of the form of chemical energy that is used in the steam-generating part. Furthermore, since the temperature-regulating material also resists the passage of steam, the material used for the temperature-regulating material and its thickness, etc., is selected so that the desired amount of steam will be released from the surface of the steam-generating unit when temperature is controlled by using a temperature-regulating material.

Another mode of controlling temperature is to make a space between the steam-generating part and the site on the skin or mucous membranes to which the steam-generating unit is applied. This type of space should be made so that there is a distance of 5 mm or longer between the steam generating part and the skin or mucous membrane. If this distance is less than 5 mm, temperature control is likely to be insufficient and the skin or mucous membranes might be burned. This type of space can be formed by a plastic molded body, etc., with good shape retention.

Other modes for temperature control can be selected as needed in accordance with the reaction of the chemical energy in the steam-generating part, etc. For example, reaction speed adjusted by varying the amount of reactants that react at the steam-generating part and the particle diameter when the reactants are particles, etc., and thereby controlling the temperature of the steam that is released from the steam-generating unit surface.

In more concrete terms, when a steam-generating composition that utilizes the heat of oxidation of iron powder at the; steam-generating part is used, in order to control the temperature of the steam that is released from the steam-generating unit surface at 50° C. or lower, the preferable amount of iron powder present per 1 $cm^2$ surface of the steam-generating unit which is applied to the skin or mucous membranes depends on the particle diameter, specific surface area, etc., of the iron powder. 0.1 $g/cm^2$ or less is preferred when the iron powder for a general chemical pocket heater is used.

In terms of the effect of providing steam to the skin and mucous membranes, the amount of steam that is released from the surface of the steam-generating unit applied to the skin or mucous membranes should be 0.01 $mg/cm^2$·min or more, particularly 0.5 $mg/cm^2$·min or more in the present invention. Furthermore, this amount of steam released is calculated by the following formula, where $Wt_0$ (g) serves as weight when the determinations are started, $Wt_{15}$ (g) serves as weight after 15 minutes, and S ($cm^2$) serves as the surface area of the part where the surface of the steam-generating unit is applied to the skin or mucous membranes, when the steam-generating unit is placed directly on a top-pan scale capable of measuring up to 1 mg units under atmosphere in a room temperature environment (20° C., 65% RH) and weight is determined 15 minutes later.

Amount of steam released ($mg/cm^2$·min)

$$=(Wt_0-Wt_{15})\cdot 1000/15S \qquad (1)$$

In order to bring the amount of steam that is released from the surface of the steam-generating unit applied to the skin or the mucous membranes to 0.01 $mg/cm^2$·min or more, particularly, 0.5 $mg/cm^2$·min or more, the surface of the steam-generating unit applied to the skin or mucous membranes is made from a moisture-permeable sheet. The moisture permeationiby ASTM methods of this moisture-permeable sheet should be 4,000 $g\cdot m^2\cdot 24$ h or more, preferably 8,000 $g/m^2\cdot 24$ h or more.

A preferred mode of the present invention is described below in detail while referring to the figures. The same symbols represent the same or identical structural elements in each of the figures.

Figure 1B:
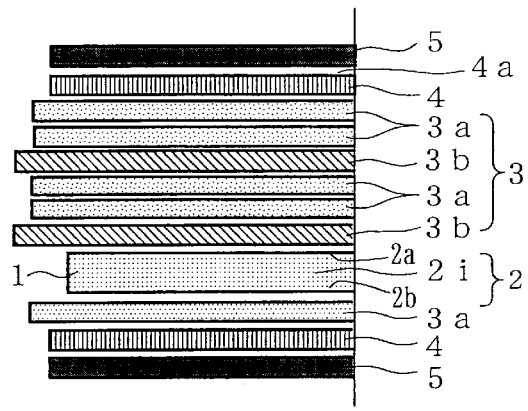

FIGS. 1A and 1B are a top view and its x—x cross section of a steam-generating unit 10A of one mode of the present invention where a temperature-regulating material has been placed in between the steam-generating part and the surface of the steam-.generating unit in order to keep the temperature of the steam released from the surface of the steam-generating unit at 50° C. or lower.

This steam-generating unit 10A comprises a steam-generating part 2 where a steam-generating composition 1 is held inside a moisture-permeable inner bag 2i, a temperature-regulating material 3 piled on the steam-generating part 2, a moisture-permeable outer bag 4 holding all of these, and further outside of these, a sealed bag 5 in which these are sealed.

This steam-generating unit 10A is used by tearing the sealed bag 5 at the time of use and taking out its contents and applying the steam-generating surface 4a of this moisture-permeable outer bag 4 to the skin or mucous membranes.

Here, steam-generating composition 1 held inside the moisture-permeable inner bag 2i is made from a composition containing the same metal powder (iron, aluminum, zinc, copper, etc.), salts (sodium chloride, potassium chloride, calcium chloride, magnesium chloride, etc.) and water as the exothermic composition used for conventional chemical pocket heaters by conventional methods and generates steam as a result of the oxidation reaction of the metal powder. Of these, iron powder is preferred as the metal powder in terms of economics, reactivity and safety. Moreover, the steam-generating composition 1 can also contain a variety of components, such as moisture-retaining agents (vermiculite, calcium silicate, silica gel, silica porous substances, alumina, pulp, wood powder, water-absorbing polymers, etc.) and reaction promoters (activated carbon, carbon black, graphite, etc.), etc.

The amount of steam-generating composition 1 held inside the moisture-permeable inner bag 2i is determined as needed in accordance with the desired amount of steam release and the steam temperature.

The surface on at least the side of the moisture-permeable inner bag 2i that touches the body (steam-generating surface 2a) is made from a moisture-permeable sheet. A sheet with a moisture permeation by ASTM methods of preferably 4,000 $g/m^2\cdot 24$ h or higher, more preferably 8,000 $g/m^2\cdot 24$ h or higher, from which the steam-generating composition 1 will not leak is used as the moisture-permeable sheet.

Actual examples are fabric, nonwoven fabric, paper, synthetic paper, etc., of one or a mixture of two or more selected from artificial fibers, such as nylon, vinylon, polyester, rayon, acetate, acrylic, polyethylene, polypropylene, polyvinyl chloride, etc., and natural fibers, such as pulp, cotton, flax, silk, animal hair, etc. Moreover, gas impermeable films or sheets (such as polyethylene, polypropylene, polyamide, polyester, polyvinyl chloride, polyvinylidene chloride, polyurethane, polystyrene, ethylene-vinyl acetate copolymer saponification product, ethylene-vinyl acetate copolymer, natural rubber, rebuilt rubber, synthetic rubber, etc.) with micropores can also be used.

On the other hand, a surface 2b on the opposite side of the steam-generating surface 2a of the moisture-permeable inner bag 2i of this steam-generating unit 10A is made from a moisture-impermeable material. By making one side 2b of the moisture-permeable bag moisture impermeable in this way, it is possible to keep the steam that has been released from the steam-generating composition 1 dispersing in the regulated direction so that the steam will pass through the steam-generating surface 2a and be effectively guided toward the body.

This moisture-impermeable surface 2b is affixed to a nonwoven 3a as the anchoring tool and the moisture-permeable inner bag 2i is thereby anchored.

The temperature-regulating material 3 piled on the steam-generating surface 2a of the moisture-permeable inner bag 2i is placed so that the temperature of the steam released from the steam-generating composition 1 at the surface of the steam-generating unit 10A (a surface (steam-generating surface 4a) of the moisture-permeable outer bag 4 on the side applied to the skin or mucous membranes) is held at 50° C. or lower, preferably 45° C. or lower, particularly 38 to 42° C., with reliability and stability. At least one of (1) fabrics or nonwoven fabrics and (2) papers, such as paper, synthetic paper, etc., given as examples of the moisture-permeable material of the moisture-permeable inner bag 2i, as well as (3) porous films or porous sheets made from plastic, natural rubber, rebuilt rubber, and synthetic rubber, (4) foamed plastics, such as urethane foam, etc., with through holes, and (5) metal foils, such as aluminum foil, etc., with through holes can be used as the structural material for this temperature-regulating material 3.

The temperature-regulating material 3 also has a moisture permeability by ASTM methods of preferably 4,000 $g/m^2\cdot 24$ h or more, more preferably 8,000 $g/m^2\cdot 24$ h or more, from which the steam-generating composition 1 will not leak out.

Thickness of the temperature-regulating material 3, each of the structural element materials forming the temperature-regulating material 3, their combined state when several structural elements are piled, the piling method, etc., are determined so that a specific amount of steam at a specific, temperature can be applied to the skin or mucous membranes.

For instance, as shown in FIG. 1B, by piling 4 pieces of nonwoven 3a and 2 pieces of paper 3b as the temperature-regulating material 3, the desired temperature control is achieved.

In place of the above temperature-regulating material 3, the moisture-permeable inner bag 2i may have additional function same as the temperature-regulating material 3.

The moisture-permeable outer bag 4 holds all of the above-mentioned moisture-permeable inner bag 2i and the temperature-regulating material 3, and an adhesive layer 9 is placed to the end of the surface (steam-generating surface 4a) of the moisture-permeable outer bag 4 on the side applied to the skin or mucous membranes. Thus, it is possible to easily fix the steam-generating unit 10A to the body when the steam-generating unit 10A is applied to the body.

Figure 2A:
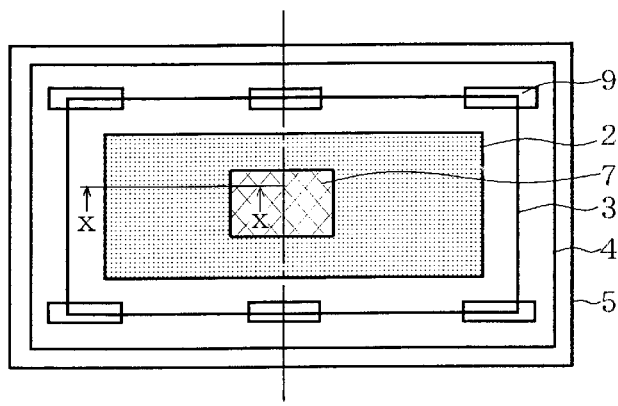
FIG. 2A is a top view of the steam-generating unit and FIG. 2B is a cross section of it.
Figure 2B:
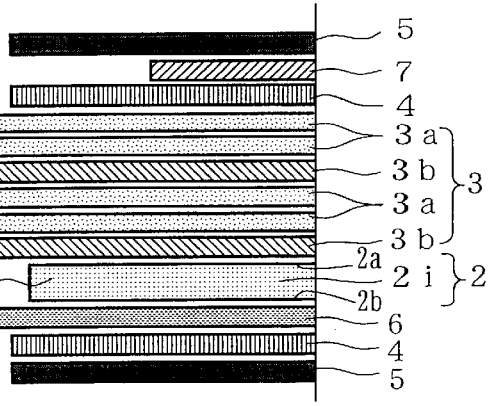

FIGS. 2A and 2B show the top view and the cross section of a steam-generating unit 10B of the present invention with a mode different from the above-mentioned. This steam-generating unit 10B has a layer (referred to below as a drug layer 7) containing cosmetic components or drugs, such as moisturizer, poultice, anti-inflammatory, exfoliating agent, depilatory, etc., is placed on the surface of the moisture-permeable outer bag 4 that comes into contact with the skin when this steam-generating unit 10B is applied to the skin. When the drug layer 7 is made in this way, it is possible for the cosmetic component or drug to effectively act on the skin with the steam and optimal heat released from the steam-generating composition 1. Furthermore, the drug layer 7 will be moistened by perspiration from the skin. However, the steam that is released from the steam-generating composition 1 will very quickly bring the drug layer 7 to a thoroughly moist state when compared to the steam that is produced by perspiration from the skin and this moist state will be retained for a longer period of time. Therefore, when compared to simply applying cosmetic components and drugs to the skin as with conventional poultices, or applying cosmetic components or drugs to the skin in combination with a simple exothermic unit that in the end does not provide steam, the release of drugs or cosmetic components from the drug layer 7 is increased by using this steam-generating unit 10B and these cosmetic components and drugs can work more effectively on the skin.

The moisturizer that forms the drug layer 7 here is, for instance, a polyol such as glycerin, etc., a ceramide, collagen, etc. When the drug layer 7 formed of these moisturizer is applied to the skin around the eyes, mouth, etc., that can easily wrinkle, the moisturizing activity of the moisturizer is enhanced by synergism of these moisturizers and the water provided from the steam-generating composition 1 and texture of the skin becomes moist and supple.

Moreover, indomethacin and methyl salicylate, etc., can be mentioned as examples of anti-inflammatories. Percutaneous absorption of these anti-inflammatories are promoted by the water, heat and the hydrating effects provided from the steam-generating composition 1. Consequently, it is possible to effectively improve myalgia, arthralgia, lumbago, etc. Of the anti-inflammatories, indomethacin is particularly preferred in terms of the large improvement in percutaneous absorption in the presence of steam.

Proteases, such as papain, etc., can be given as examples of exfoliating agents. This protease can be fixed to the surface of the moisture-permeable outer bag 4 by conventional methods when the solid enzyme is prepared. The catalytic activity of this type of solid protease is improved by the heat and moisture provided from the steam-generating composition 1. Consequently, residual skin layers can be removed from the elbows, knees, heels, etc.

Depilatory components such as calcium thioglycolate, etc., are examples of depilatories. The steam that is provided from the steam-generating composition 1 humidifies and softens the area around the hair root and therefore, by using depilatory in this way, the pain that accompanies hair removal can be alleviated and better depilatory results than when conventional depilatories are employed can be obtained.

The steam-generating unit 10B in FIGS. 2A and 2B differs from the steam-generating unit 10A in FIGS. 1A and 1B in that it has the drug layer 7 and further, both of the steam-generating surface 2a and the surface 2b on the opposite side, of the moisture-permeable inner bag 2i are made from a moisture-permeable material, and a moisture-impermeable sheet 6, for instance, a piled sheet of ethylene-vinyl acetate copolymer and polyethylene, is piled on the surface 2b on the opposite side of the steam-generating surface 2a. Thus, dispersing of the steam that has been released from the steam-generating composition 1 is prevented by using this moisture-impermeable sheet 6 and the steam can pass through the steam-generating surface 2a of the moisture-permeable inner bag 2i and be more effectively guided toward the body.

Figure 3A:
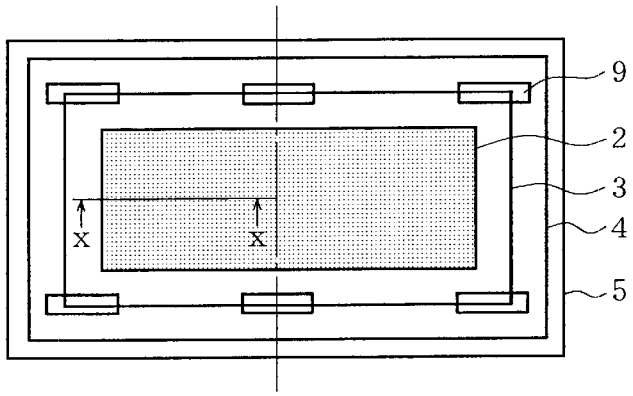
FIG. 3A is a top view of the steam-generating unit and FIG. 3B is a cross section of it.
Figure 3B:
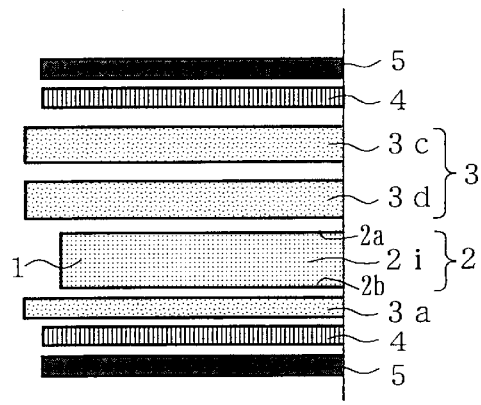

FIGS. 3A and 3B are a top view and a cross section of a steam-generating unit 10C of the present invention with yet another mode. The steam-generating units in above-mentioned FIGS. 1 and 2 used 4 pieces of nonwoven 3a and 2 pieces of paper 3b piled together for the temperature-regulating material 3, but in FIG. 3, two pieces of nonwoven (3c, 3d) are combined together and piled.

Figure 4A:
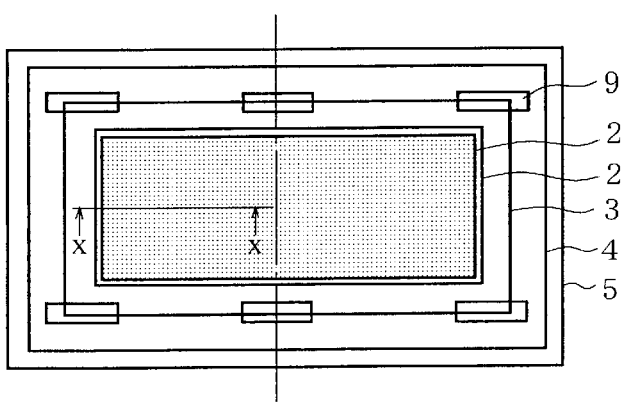
FIG. 4A is a top view of the steam-generating unit and FIG. 4B is a cross section of it.
Figure 4B:
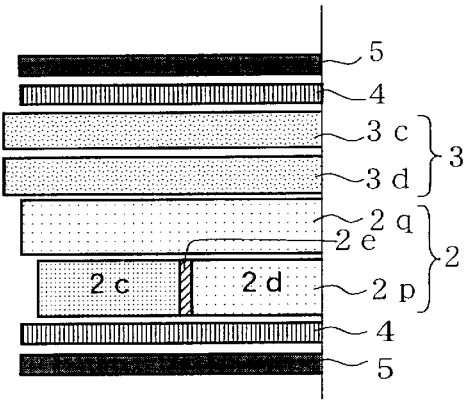

FIGS. 4A and 4B are a top view and a cross section of a steam-generating unit 10D of the present invention of still a different mode. In the above-mentioned 3 steam-generating units 10A, 10B and 10C, the heat of oxidation of metal powder from a conventional chemical pocket heater composition is used in the steam-generating part 2, but the heat of hydration of calcium chloride is used in the steam-generating part 2 of the steam-generating unit 10D of FIG. 4.

The steam-generating part 2 of this steam-generating unit 10D is made from a heating part 2p and a vaporizing part 2q. The heating part 2p comprises polyethylene film, which is water impermeable, and the inside is divided into 2 receptacles 2c and 2d. After introducing the contents to these receptacles 2c and 2d, these 2 receptacles 2c and 2d are pressed to be easily connected with one another at their boundary region 2e. Calcium chloride is introduced to one of these (receptacle 2c), while water is introduced to the other (receptacle 2d). The vaporizing part 2q is constructed by a nonwoven with a water-absorbed polymer as the middle layer and placing this in a nonwoven inner bag made from moisture-permeable and water-impermeable polypropylene fibers.

Figure 5A:
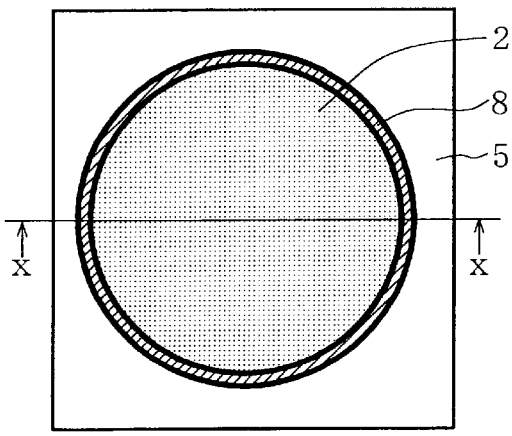
FIG. 5A is a top view of the steam-generating unit and FIG. 5B is a cross section of it.
Figure 5B:
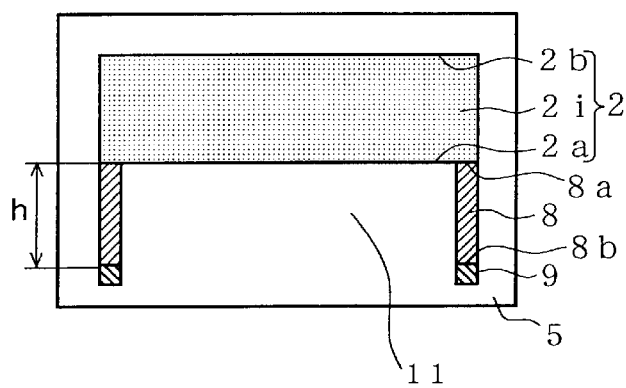

FIGS. 5A and 5B are a top view and a cross section of a steam-generating unit 10E of one mode of the present invention where there is space 11 in between the steam-generating part and the part applied to the skin or mucous membranes in order to control the temperature to 50° C. or lower. The same steam-generating part 2 of the steam-generating unit 10E as in FIG. 1 is used. A support 8 of the space 11 is made from a cylindrical polypropylene molded article. One end, 8a, is placed to the steam-generating part 2, while the other end 8b is patched to the skin or mucous membranes by adhesive layer 9. Height h of the cylinder of the support 8 should be 5 mm or higher. If height h is under 5 mm, temperature control will be insufficient and burns may occur.

Figure 6A:
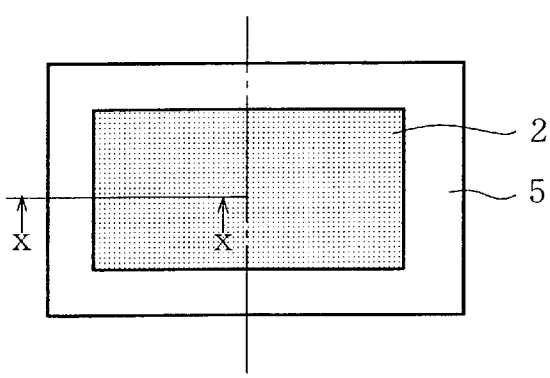
FIG. 6A is a top view of the steam-generating unit and FIG. 6B is a cross section of it.
Figure 6B:
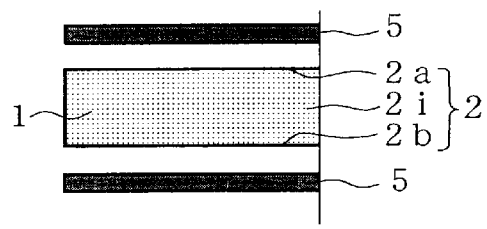

FIGS. 6A and 6B are a top view and a cross section of yet another steam-generating unit 10F of the present invention. The amount of iron powder that is present per 1 cm² surface of the steam-generating unit applied to the skin or mucous membranes is low in this steam-generating unit 10F when compared to above-mentioned steam-generating unit 10A (FIG. 1), 10B (FIG. 2), 10C (FIG. 3), and 10E (FIG. 5) and therefore, the temperature of the steam at the surface of the steam-generating unit 10F is kept to 50° C. or lower without placing a temperature-regulating material or space between the skin or mucous membranes and the steam-generating part 2 when it is applied to said skin or mucous membranes.

Figure 7:
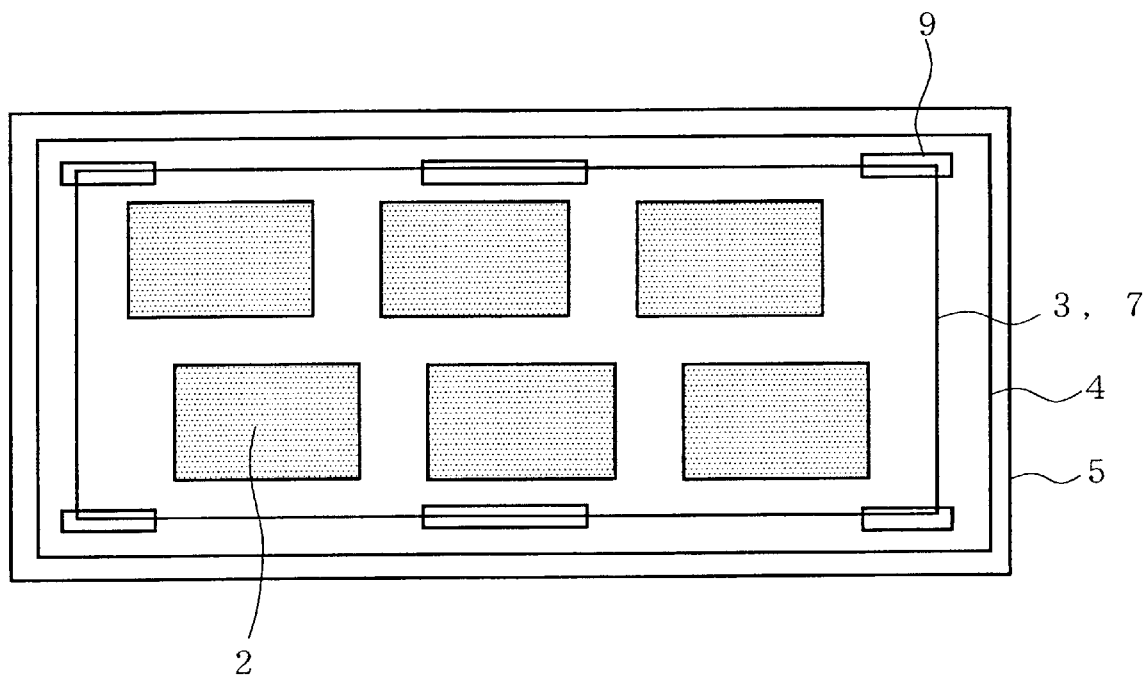
FIG. 7 is a top view of the steam-generating unit.

FIG. 7 is a top view of yet another steam-generating unit 10G of the present invention. By means of the above-mentioned steam-generating unit 10A (FIGS. 1A and 1B), almost the entire surface is placed on the steam-generating part 2, but by means of the steam-generating unit 10G of FIG. 7, several steam generating parts 2 are placed with a space between steam-generating parts 2, inside the steam-generating unit 10G. Thus, it seems that even if steam-generating parts 2 are placed with a space inside the steam-generating unit 10G, steam is generated and cosmetic component or drug is released almost uniformly from the steam-generating unit 10G.

Consequently, in the steam-generating unit of the present invention, there are no special restrictions to the position of the steam-generating parts inside the steam-generating unit.

Various modes of the present invention other than those illustrated above can be used as long as the temperature of the steam released from the steam-generating unit surface is controlled to 50° C. or lower. For instance, by means of the steam-generating unit 10B in FIGS. 2A and 2B, the drug layer 7 containing cosmetic component or drug is placed at the outer surface of the moisture-permeable outer bag 4, but the drug layer 7 can also be placed between the steam-generating part 2 and the moisture-permeable outer bag 4. Moreover, the adhesive layer 9 on the moisture-permeable outer bag 4 can be formed over one entire side of the moisture-permeable outer bag 4, and cosmetic component or drug can also be contained in the adhesive layer 9.

EXAMPLES

The present invention is described below in concrete terms with examples.

Example 1

The steam-generating unit 10A of the mode in FIGS. 1A and 1B was made as follows:

First, 5 g of a mixture of 1 part by weight water-absorbing polymer (Nihon Shokubai Co., Ltd., brand name: Aqualik CA), 3 parts by weight silica gel (Wako Junyaku Co., Ltd., brand name: Wakogel C-200), and 10 parts by weight of aqueous 12.5 wt % sodium chloride solution and 10 g iron powder (Dowa Teppun Kogyo Co., Ltd., brand name: RKH) were mixed to obtain the steam-generating composition 1.

Three grams of this steam-generating composition 1 were then packed into a 3×3 cm² small square bag comprising a vinyl-coated sheet on one side (Nitto Denko Co., Ltd., brand name: Nitotack) and a sheet of moisture-permeable nonwoven (Mitsui Kagaku, brand name: Syntex MB, net: 15 g/m²) on the other side.

This small bag was placed and anchored on its bottom surface to the nonwoven 3a (Chisso Co., Ltd., brand name: Air-raid, net: 24 g/m²) served as the support, with the surface made from moisture-permeable nonwoven facing up. The temperature-regulating material 3 with the piled structure in FIG. 1, that is, 1 layer of paper 3b (Kreshia, brand name: Kimtowel), 2 layers of nonwoven 3a (Chisso, brand name: Air-raid, net: 24 g/m²), 1 layer of paper 3b (Kreshia, brand name: Kimtowel), and 2 layers nonwoven 3a (Chisso Co., Ltd., brand name: Air-raid, net: 24 g/m²) were piled in order, and the entire unit was then placed in the moisture-permeable outer bag 4 comprising moisture-permeable nonwoven (Mitsui Kagaku, brand name: Syntex MB, net: 15 g/m²). Then the entire outside was sealed by an air-tight bag (sealed bag) 5 (Asahi Kasei Polyplex Co., Ltd., brand name: Hiryu) to obtain the steam-generating unit 10A.

Example 2

A steam-generating unit 10B of the mode shown in FIGS. 2A and 2B was made as follows:

Three grams of the same steam-generating composition 1 as in Example 1 were packed in a 3×3 cm² small square bag made from moisture-permeable nonwoven (Mitsui Kagaku, brand name: Syntex MB, net: 15 g/m²). This small bag was placed and fastened to the moisture-impermeable sheet 6 that was a pile of ethylene-vinyl acetate copolymer and polyethylene, and the temperature-regulating material 3 same as Example 1 (one layer of paper 3b, 2 layers of nonwoven 3a, 1 layer of paper 3b, and 2 layers of nonwoven 3a piled in succession) were placed on the other side and the entire unit was introduced to the outer bag 4 made from moisture-permeable nonwoven (Syntex MB, net: 15 g/m²). An adhesive layer 9 (Nichiban Co., Ltd., brand name: Nicetack) was placed around the periphery of this surface and filter paper (the drug layer 7) holding methyl salicylate was set in the middle of this. The entire outside was sealed with the air-tight bag 5 (Asahi Kasei Polyflex, brand name Hiryu) to obtain the steam-generating unit 10B.

Example 3

A steam-generating unit 10C with the mode in FIGS. 3A and 3B was made as follows:

Three grams of the same exothermic composition 1 as in Example 1 were packed in a 3×3 cm² small square bag made from a vinyl coated sheet (Nitto Denko Co., Ltd., brand name: Nitotack) on one side and a moisture-permeable nonwoven (Mitsui Kagaku, brand name: Syntex MB, net: 15 g/m²) on the other side. This small bag was placed and anchored on its bottom surface to the nonwoven 3a (Chisso Co., Ltd., brand name: Air-raid, net: 24 g/m²) served as the support, with the surface of the moisture-permeable non-woven facing up. Then the temperature-regulating material 3 with the piled structure in FIG. 3 (pile of 2 layers nonwoven 3c (Honshu Kinocloth Co., Ltd., brand name: Kinocloth KS-40) and 3d (Nihon Bairin Co., Ltd., brand name; Baiwarm Airback KNF-350)) was placed on top of this and the entire unit was placed in outer bag 4 comprising moisture-permeable nonwoven (Syntex MB, net: 15 g/m²). The adhesive layer 9 (Nichiban Co., Ltd., brand name: Nicetack) was placed on parts of this surface and the entire unit was sealed on the outside with the air-tight bag 5 (Asahi Kasei Polyflex, brand name: Hiryu) to obtain the steam-generating unit 10C.

Example 4

A steam-generating unit 10D with the mode in FIGS. 4A and 4B was made as follows:

Calcium chloride was introduced to one receptacle 2c, of a bag comprising polyethylene film, which is water impermeable, that had been made by dividing the inside into 2 receptacles 2c and 2d, as shown in FIG. 4, so that these 2 receptacles 2c and 2d can be easily connected at a boundary 2e when they are pressed, while water was introduced to the other receptacle 2d, to form the heating part 2p. Nonwoven (Honshu Kinocloth Co., Ltd., brand name: B-SAP85) impregnated with 20 g water was placed on top of the heating part 2p as the vaporizing part 2q. The temperature-regulating material 3 with the piled structure in FIG. 3 (pile of nonwoven 3c (Honshu Kinocloth Co., Ltd., brand name: Kinocloth KS-40) and 3d (Nihon Bairin Co., Ltd., brand name: Baiwarm Airback KNF-350)) was further placed on top of this and the entire unit was housed in the outer bag 4 comprising moisture-permeable nonwoven (Mitsui Kagaku, brand name: Syntex MB, net: 15 g/m$^2$). The adhesive layer 9 (Nichiban Co., Ltd., brand name: Nicestack) was placed on parts of this surface and the entire unit was further sealed on the outside by the air-tight bag 5 (Asahi Kasei Polyflex Co., Ltd., brand name: Hiryo) to obtain steam-generating unit 10D.

Example 5

A steam-generating unit 10E of the mode in FIGS. 5A and 5B was made as follows:

Three grams of the same steam-generating composition 1 as in Example 1 were packed in a small round bag (the moisture-permeable inner bag 2i) with a diameter of 30 mm comprising a vinyl coated sheet (Nitto Denko, brand name: Nitotack) on one side (2b) and moisture-permeable nonwoven (Mitsui Kagaku, brand name: Syntex MB, net: 15 g/m$^2$) on the other side (2a). Then, with the vinyl-coated surface of this small bag facing up, polypropylene cylindrical molded article (the support 8) with a diameter of 30 mm and height (h) of 6 mm was placed on the bottom of the small bag, and the adhesive layer 9 was further placed so that the product could be patched to the skin or mucous membranes. The entire unit was further sealed on the outside with the air-tight bag 5 (Asahi Kasei Polyflex Co., Ltd., brand name Hiryu) to obtain the steam-generating unit 10E.

Examples 6 through 10

Steam-generating units 10F-1, 10F-2, 10F-3, 10F-4, and 10F-5 of the mode in FIGS. 6A and 6B were made as follows:

The exothermic compositions in Table 1 were each prepared and then these were packed, in the amounts shown in Table 1, in a 5×5 cm$^2$ small square bag comprising a gas-permeable composite sheet (Nitto Denko, brand name Breslon 38) on one side and moisture-permeable nonwoven (Mitsui Kagaku, brand name: Syntex BM, net: 15 g/m$^2$) on the other side. Amounts of iron powder per 1 cm$^2$ surface of these steam-generating units are also listed in Table 1.

Furthermore, the entire unit was sealed on the outside with the air-tight bag 5 (Asahi Kasei Polyflex Co., Ltd., brand name: Hiryu) to obtain steam-generating units 10F-1, 10F-2, 10F-3, 10F-4, and 10F-5.

TABLE 1

| Example | 6 | 7 | 8 | 9 | 10 |
|---|---|---|---|---|---|
| Steam-generating unit | 10F-1 | 10F-2 | 10F-3 | 10F-4 | 10F-5 |
| Composition (wt %) | | | | | |
| Iron powder[*1] | 33.3 | 25.0 | 25.0 | 31.7 | 28.6 |
| water-absorbing polymer[*2] | — | — | 9.4 | 15.7 | 8.9 |
| Calcium silicate micropowder | 16.7 | 18.8 | 9.4 | 8.1 | 8.9 |
| Aqueous 15% sodium chloride solution | 50 | 56.2 | 56.2 | 44.5 | 53.6 |
| Amount packed in bag (g) | 6.0 | 8.0 | 8.0 | 6.3 | 6.3 |
| Amount of iron powder (g/cm$^2$) | 0.080 | 0.080 | 0.080 | 0.080 | 0.072 |

[*1]Dowa Teppun Kogyo Co., Ltd., brand name: RKH
[*2]Nihon Shokubai Co., Ltd., brand name: Aqualik CA

Evaluations

The steam-generating unit obtained in each of the examples was taken out from the air-tight bag 5 and maximum temperature of the steam released from the steam-generating unit surface (referred to below as maximum steam temperature) was found in accordance with the temperature determination method in JIS S4100 (method *3 in Table2). Furthermore, in Example 1, maximum temperature was also found by the above-mentioned method of setting the detector of a temperature gauge on the surface of the steam-generating unit (method *4 in Table2).

In addition, the amount of steam released per unit time and unit surface area by the steam-generating unit obtained from each Example was found by above-mentioned formula (1). The results are listed in Table 2.

Moreover, the maximum steam temperature and amount of steam released were also found for commercial chemical pocket heaters A, B and C and the product of an example from Japanese Patent Laid-Open No. 62-172907 as Comparative Examples 1 through 4. The results are listed in Table 2.

TABLE 2

| | Maximum steam temperature (method*3) (° C.) | Maximum steam temperature (method*4) (° C.) | Amount of steam released (mg/cm$^2$ · min) |
|---|---|---|---|
| Example 1 (10A) | 47 | 42 | 1.10 |
| Example 2 (10B) | 47 | — | 1.10 |
| Example 3 (10C) | 48 | — | 1.67 |
| Example 4 (10D) | 48 | — | 0.83 |
| Example 5 (10E) | 49 | — | 1.98 |
| Example 6 (10F-1) | 47 | — | 1.60 |
| Example 7 (10F-2) | 48 | — | 1.63 |
| Example 8 (10F-3) | 46 | — | 1.43 |
| Example 9 (10F-4) | 46 | — | 1.33 |
| Example 10 (10F-5) | 44 | — | 0.80 |
| Comparative Example 1 (Commercial product A) | 50 | — | <0.01 |
| Comparative Example 2 (Commercial product B) | 46 | — | <0.01 |
| Comparative Example 3 (Commercial product C)[*5] | 41 | — | <0.01 |
| Comparative Example 4 (Japanese Patent Laid-Open No. 62-172907 Example product) | 84 | — | 2.80 |

[*5]Medical heating tool that is patched directly to the skin.

As is clear from Table 2, almost no steam was generated by commercial chemical pocket heaters (Comparative Examples 1 through 3). Moreover, although steam was definitely generated by Comparative Example 4, the maximum steam temperature rose to 84° C. and therefore, it could not be used on the skin or mucous membranes. In contrast to this, the steam generated by the steam-generating units of the present invention was at a moderate temperature of 50° C. or lower and therefore, warm steam can be easily provided to the skin and mucous membranes.

INDUSTRIAL APPLICABILITY

By means of the present invention, steam that is as safe as that from a steam towel can be continuously supplied to the skin and mucous membranes by a simple structure that uses chemical energy.

What is claimed is:

1. A steam-generating unit, comprising:
   i) a steam-generating part that uses chemical energy,
   ii) a moisture-permeable sheet; and
   iii) a temperature-regulating material disposed between said steam-generating part and said moisture-permeable sheet,
   wherein the amount of steam released from a surface of said steam-generating unit which is applied to skin or mucous membranes is 0.01 mg/cm$^2$·min or more, and
   a temperature of said steam released from said surface of said steam-generating unit, is 50° C. or lower.

2. The steam-generating unit according to claim 1, wherein the amount of steam released from the surface of the steam-generating unit applied to the skin or the mucous membranes is 0.5 mg/cm$^2$·min or more.

3. The steam-generating unit according to claim 1, wherein there is cosmetic component or drug at the surface or inside of the steam-generating unit and said cosmetic component or drug is released with the steam.

4. The steam-generating unit according to claim 1, wherein an adhesive layer is formed on the surface of the steam-generating unit to be applied to the skin.

5. The steam-generating unit according to claim 4, wherein cosmetic component or drug is contained in the adhesive layer.

6. The steam-generating unit according to claims 1, wherein the steam-generating part comprises a steam-generating composition that contains metal powder, salts, and water, and that releases steam with oxidation of the metal powder.

7. The steam-generating unit according to claim 6, wherein there is a structure of at least one of (1) fabric or nonwoven fabric, (2) paper, (3) porous film or porous sheet molded from plastic, natural rubber, rebuilt rubber, or synthetic rubber, (4) foamed plastic with through-holes, and (5) metal foil with through-holes, as the temperature-regulating material that keeps the temperature of the steam released by the steam-generating part to 50° C. or lower on the outside of the steam-generating part.

* * * * *